United States Patent [19]
Widder et al.

[11] Patent Number: 5,315,997
[45] Date of Patent: May 31, 1994

[54] METHOD OF MAGNETIC RESONANCE IMAGING USING DIAMAGNETIC CONTRAST

[75] Inventors: Kenneth J. Widder, Del Mar; James L. Barnhart, Encinitas, both of Calif.

[73] Assignee: Molecular Biosystems, Inc., San Diego, Calif.

[21] Appl. No.: 929,997

[22] Filed: Aug. 13, 1992

Related U.S. Application Data

[63] Continuation-in-part of Ser. No. 540,504, Jun. 19, 1990.

[51] Int. Cl.$^5$ .............................................. A61B 5/055
[52] U.S. Cl. ............................... 128/653.3; 128/653.4; 424/9
[58] Field of Search ............... 128/653.2, 653.3, 653.4; 424/9

[56] References Cited

U.S. PATENT DOCUMENTS 4,657,756  4/1987  Rasor et al. ............................... 424/9
4,775,522  10/1988  Clark, Jr. ................................... 424/9

OTHER PUBLICATIONS

Lufkin, "Magnetic Resonance Image Formation", pp. 42–79.

*Primary Examiner*—Ruth S. Smith
*Attorney, Agent, or Firm*—Morrison & Foerster

[57] ABSTRACT

A method of magnetic resonance imaging (MRI) is disclosed which employs a diamagnetic contrast agent comprising gas-carrying, microparticles, which are preferably microspheres consisting of minute gas bubbles encapsulated by stabilized biocompatible material. The MRI is carried out to produce a shortened T2* effect. The method is especially useful in imaging the vascular system as in angiography or venography.

6 Claims, No Drawings

METHOD OF MAGNETIC RESONANCE IMAGING USING DIAMAGNETIC CONTRAST

RELATED APPLICATION

This application is a continuation-in-part of copending application Ser. No. 07/540,504, filed Jun. 19, 1990 now abandoned.

FIELD OF INVENTION

The field of this invention is magnetic resonance imaging (MRI), and more particularly MRI using contrast agents.

BACKGROUND OF INVENTION

Heretofore contrast agents for improving magnetic resonance imaging of protons have consisted of magnetizable substances comprising metals or metallic compounds. Such contrast agents may be paramagnetic, ferromagnetic, or superparamagnetic, and act through dipole interactions with tissue protons. Where the substance is toxic, such as gadolinium, it can be administered in chelated form. In another kind of MRI contrast agent, ultrafine particles of a ferromagnetic or superparamagnetic material, such as magnetite ($Fe_3O_4$), have been dispersed in a biodegradable matrix material, and formed into microspheres which are capable of passing through capillaries. Such MRI contrast agents are described in U.S. Pat. Nos. 4,675,173 and 4,849,217. A preferred biodegradable material is human serum albumin. Albumin is not known to have any MRI contrast-producing properties. It is the magnetizable particles dispersed in the albumin which produces the MRI contrast effect.

It is known that gas microbubbles are strong scatterers of ultrasonic waves in fluid media, and may therefore be useful as an imaging agent for ultrasonic echographic imaging (U.S. Pat. No. 4,276,885). The preparation and use of microbubble ultrasonic imaging agents are described in U.S. Pat. Nos. 4,718,433, 4,572,203, 4,657,756 and 4,774,958. U.S. Pat. No. 4,657,756 suggests that microbubbles can alter the transmission characteristics of electromagnetic waves and therefore might have applications in "x-ray imaging (e.g., CT scanning), NMR imaging, microwave imaging, and marine sonar" (col. 3, lines 43-44). However, the patent contains no examples or other disclosure as to how such applications could be carried out.

Stabilized, concentrated gas-center microspheres in small enough diameters to pass through the capillaries are described in U.S. Pat. No. 4,844,882. A product of this kind designed for ultrasonic imaging use has been produced by Molecular Biosystems, Inc., of San Diego, Calif., and is known by the registered trademark "AL-BUNEX". Another kind of gas-carrying ultrasonic imaging particles are described in published European Patent Application 0 365 467. Gas bubbles are carried by solid particles that are small enough to pass through the capillaries.

As far as is known no one has heretofore described a method for using microbubbles as an MRI contrast agent. MRI utilizes radio frequency pulses and magnetic field gradients applied to a subject in a strong field to produce the images. The scientific principles and mechanisms involved are entirely different from ultrasonic imaging which utilizes high frequency sound waves.

There is voluminous literature on magnetic resonance imaging, and a number of United States and foreign companies manufacture equipment for experimental and clinical MRI applications. Existing knowledge in the field of contrast agents for use in MRI was surveyed in a recent treatise entitled "Enhanced Magnetic Resonance Imaging", edited by Val M. Runge (1989, C. V. Mobsy Company); and see also Peter G. Morris, "Nuclear Magnetic Imaging in Medicine and Biology", (1986, Oxford University Press). Accepted MRI terminology includes the following definitions which are applicable to this application.

MRI TERMINOLOGY

Artifacts—Undesirable features in NMR images which do not correspond to true anatomical or pathological conditions which may be caused by non-ideal effects in the imaging process.

Echo Time (ET)—A timing parameter in an NMR pulse sequence which describes the time delay between the RF excitation pulse and acquisition of the NMR signal.

FID—Free induction decay, which is the fundamental signal detected in NMR.

FOV—Field of view.

Gradient Echo—The NMR echo signal produced when a gradient field is first applied with on polarity to destroy the NMR FID signal and then with opposite polarity to cause the signal to refocus.

Magnetic Susceptibility—The constant of proportionality which relates the degree of magnetization of a material to the strength of an applied magnetic field.

MRI—Magnetic Resonance Imaging.

NMR—Nuclear Magnetic Resonance.

Pixel—Picture Element in a digital image.

Pulse Sequence—A series of RF pulses used in conjunction with gradient magnetic fields and NMR signal reception to produce NMR images.

Repetition Time (TR)—The time to repeat parameter in an NMR pulse sequence which comprises the interval between repetitions of RF excitation pulses.

RF—Radio Frequency.

Spin Echo—The reappearance of an NMR signal after the free induction decay has died away due to T1 and T2 effects.

T1—Spin-lattice relaxation time or longitudinal relaxation time which is the characteristic time constant for spins to tend to align themselves with an external magnetic field.

T2—Spin-spin or transverse relaxation time which is the characteristic time constant for loss of phase coherence among spins oriented at an angle to a static magnetic field.

T2*—The apparent transverse relaxation time which combines the true T2 of a sample with additional factors producing a loss of phase coherence of the NMR signal; such as magnetic field inhomogeneities.

T1-Weighted—An MR image which is made using pulse sequence parameters which emphasize differences in the T1 of the subject.

T2-Weighted—An MR image which is made using pulse sequence parameters which emphasize differences in the T2 of the subject.

Telsa (T)—Unit of magnetic field strength equivalent to one Newton per ampere meter.

MRI ANGIOGRAPHY

In a recent paper, Majumdar, et al. stated: "NMR images that portray blood flow at the capillary level would likely have widespread clinical application" (*Mag. Res. Imag.*, 6:611-615, 1988). However, as the authors pointed out: "Methods designed to portray perfusion effects, such as conventional spin echo magnitude or phase maps, have thus far enjoyed only limited success." As further stated: "A primary limitation on the sensitivity of such methods is the small size of the blood to background NMR signal ratio, which arises from the fact that blood comprises only a small fraction of tissue protons."

Majumdar, et al. reported on their investigation of superparamagnetic particles as an MRI contrast agent in blood. They pointed out that if the effect of the superparamagnetic particles was confined to the blood only a limited T1 or T2 relaxation would be expected. They concluded: "For tissue protons to experience T2 shortening through dipolar interactions with paramagnetic ions, tissue water must diffuse into the immediate hydration sphere of an ion in the time TE in a spin echo sequence in order to experience the local field of the ion" (Majumdar, et al. cited above, page 611).

MR angiography was discussed by Lee, et al., *Mag. Res. Med.*, 12:113, 1989, stating that clinical images have been produced without a contrast agent. The observed contrast was caused by the dephasing of blood moving along the readout gradient.

SUMMARY OF INVENTION

The method of magnetic resonance imaging of this invention, which is particularly applicable for vascular system imaging, employs a diamagnetic contrast agent. The diamagnetic agent comprises gas-carrying, non-magnetic microparticles predominantly of diameters less than 8 microns. This contrast agent is introduced into the blood before or during the MRI examination. When the diamagnetic agent reaches the site to be imaged, MRI imaging is carried out by a T2-weighted or T2*-weighted technique. The portion of the blood containing the diamagnetic imaging agent is contrasted by its difference in magnetic susceptibility. This is caused by the gas bubbles producing magnetic susceptibility gradients which result in a shortened T2*. The segment of blood being imaged with the assistance of the diamagnetic contrast agent will experience an enhanced signal loss and will appear dark against the surrounding tissues.

The method of this invention can be used for examinations of the circulatory system for pathological conditions which may exist in the capillaries, in the heart or in the arteries or veins. Specifically, it is expected that angiograms and venograms of clinical image quality can be obtained.

DETAILED DESCRIPTION

The method of this invention can be practiced with gas-microbubbles, which may be encapsulated by non-magnetic materials, or which are associated with particulates which are non-magnetic. Diamagnetic imaging agents for use in the method of this invention comprise gas-carrying, non-magnetic microparticles which are predominately of less than 8 microns diameter so they can pass through capillaries. For example, such microbubbles may be produced and administered as described in U.S. Pat. Nos. 4,572,203 and 4,718,433. (For other methods of microbubble generation, see Schlepper, *Amer. Heart J.*, 115:399-408, 1988; and Butler, et al., *Ultrasound Imaging*, 12:150, Abst. 9.2, 1990.)

The magnetic resonance imaging method of this invention preferably employs microspheres consisting of gas microbubbles encapsulated by a stabilized biocompatible material. The "ALBUNEX" microspheres of Molecular Biosystems, Inc. are an example of the kind of imaging agent which can be used most effectively in the method of this invention. Neither the microsphere contrast agent nor the blood or tissues being imaged are magnetic substances. They are diamagnetic. Nevertheless, image contrast effects can be obtained because of differences in magnetic susceptibility.

As indicated, the MRI method of this invention involves magnetic susceptibility effects. Such effects have been discussed in the literature primarily as a problem to be overcome or avoided. As stated in "Enhanced Magnetic Resonance Imaging", (cited above) at pages 35 to 36: "Abrupt changes in magnetic susceptibility distort the magnetic field locally, like any other static magnetic field inhomogeneitity. As a result, the shape of anatomic structures can become warped in both spin-echo and gradient-echo techniques." Large air filled cavities in the body such as the sinus or bowel can result in reduced image intensity due to a magnetic susceptibility effects. Ludeke, et al., *Mag. Res. Imag.*, 3:329-343, 1985, studied these effects using image artifacts in images of phantoms containing air. It was proposed that procedures should be used to correct image distortions caused by susceptibility variations created by air-filled cavities in the body.

Encapsulated gas-center microspheres for use in the method of this invention can be prepared as described in U.S. Pat. No. 4,844,882, or by the continuous single-stage method described in U.S. application Ser. No. 244,844, which is co-owned with the present application. A suitable product of this kind is presently described as an ultrasonic imaging agent. It is available from Molecular Biosystems, Inc. of San Diego, Calif., being called by the registered trademark "ALBUNEX".

Other microbubble preparations which can be used in the method of this invention are also available for ultrasonic imaging applications. These include aircarrying galactose particles ["Echovist", Schering AG, West Germany, as described by Fritzsch, et al., *Invest. Radiol.* (Suppl) 23:S302-S305, 1988; and, "Levovist", Schering AG, West Germany, as described by Smith, et al., *J. Am. College Cardiology*, 13:1622-1628, 1989]. The methods of manufacturing products corresponding to "Echovist" and "Levovist" are described in published European patent applications Nos. 0 035 467 and 0 122 624. For example, galactose (1988 gr.) and palmitic acid (120 gr ) are dissolved in ethanol, sterile filtered, and the solution is evaporated to dryness. The dried material is milled under aseptic conditions to a grain size in a range of 1 to 5 microns. To prepare this product for intravenous administration, the microparticles are mixed with water and shaken vigorously until a homogeneous suspension results. This causes air bubbles to become associated with the particles, being on the particle surfaces or in intracrystalline crevices.

A preferred MRI contrast agent as prepared for administration comprises a sterile aqueous medium containing a dispersion of microspheres predominately of diameters of less than 8 microns. The microspheres consist of gas microbubbles encapsulated by a stabilized biocompatible material. The preferred microspheres have centers of air surrounded by heat-insolubilized human serum albumin. Other gases can be used such as oxygen, carbon dioxide, or nitrogen. The aqueous medium may consist of an albumin solution, normal saline, or other aqueous medium suitable for intravenous injection. The medium as well as the microspheres should be sterile.

The microspheres or other gas-carrying microparticles should be of diameters less than 8 microns for easy passage through capillaries. For example, microparticles in the range from 2 to 6 microns are suitable. The "ALBUNEX" product of Molecular Biosystems, Inc. which is especially suitable for use in the method of this invention, can be prepared by sonication of a 5% aqueous solution of human serum albumin by the process of U.S. Pat. No. 4,957,656. The air-center albumin encapsulated microspheres are about 90% below 8 microns. The microspheres can be highly concentrated, such as up to $5 \times 10^8$ microspheres per milliliter. The "ALBUNEX" product has excellent stability at ordinary room temperatures; being stable from 6 to 12 months or longer. The imaging agents used in the method of this invention should contain gas-carrying particles or microspheres at concentrations of at least $1 \times 10^4$ microspheres per milliliter of imaging agent. In preferred embodiments higher concentration are used, viz. concentrations of at least $1 \times 10^6$ microspheres per milliliter.

The contrast agent is administered into the circulating blood of a human subject, or other mammal, either prior to or during the MRI examination. For example, a bolus of the imaging agent may be introduced into a vein or artery by hypodermic injection or by catheter. The introduction site may be at or close to the site where the examination is to be made. Alternatively, the imaging agent can be transferred through the bloodstream to the site of examination. The preferred microspheres are sized so that they pass readily through capillaries. It is therefore feasible to introduce the contrast agent into a peripheral vein for transfer through the circulatory system. When using imaging agents of the microsphere concentrations described above, an effective imaging amount may range from 3 to 50 milliliters, depending upon the purpose of the examination. More specifically, the amount administered may be from 3.5 to 20 milliliters when employing concentrations of at least $1 \times 10^6$ microspheres per milliliter in imaging the heart or vascular system.

The method of this invention is believed to be particularly adapted for blood flow examinations, as in angiography. The rate of blood flow and course of the administered microspheres can be directly observed. The method is therefore adapted for imaging the vasculature to produce contrast-enhanced MR angiograms.

When an imaging amount of the diamagnetic agent used in the method of this invention has reached the site to be imaged, it is preferred to carry out T2-weighted or T2*-weighted MRI imaging. The portion of the blood containing the imaging agent is thereby contrasted by its difference in magnetic susceptibility, producing a shortened T2* effect. Obtaining a T2* effect is critical for effective magnetic resonance imaging with the microbubble imaging agents used in the method of this invention. For example, an echo planar technique may be used, which utilizes a single radio frequency excitation pulse to produce a T2*-effect. Alternatively, the MR imaging may be carried out by techniques using a series of radio frequency excitation pulses in fast MRI where the time-to-repeat (TR) is substantially less than 1 second, such as less than 100 milliseconds, thereby producing a T2* effect.

Fast imaging techniques may be employed as described in "Enhanced Magnetic Resonance Imaging", Runge, Ed. (1989), cited above, at pages 31-35, which can also provide a T2* effect. For example, a fast gradient echo technique may be used with a series of radio frequency pulses and time-to-repeat (TR) of less than 100 milliseconds. A low flip angle (less than 90°) is preferably employed with gradient-reversal echos. Such techniques have been referred to generically as "FLASH" in the cited Runge treatise. Another such fast imaging technique now widely in use is known as "GRASS"; a trademark of the GE Corp. which is an acronym for Gradient Recalled Acquisition in the Steady State. The term "FLASH" is an acronym for fast-low angle shot. MRI equipment is available for practicing such techniques from General Electric Medical Systems, Milwaukee, Wis., Philips-Picker International, Inc., Highland Heights, Ohio, and other companies. With such available techniques and equipment T2 or T2* weighted sequences produce T2* effects which are needed for useful contrast imaging using a microbubble imaging agent.

As described by Bendel, *Mag. Res. Med.*, 5:366-370 (1987), "FLASH" sequences include "spoiling-Flash" as one type, and "refocusing-Flash" as another. In spoiling sequences, the coherence of transverse magnetization is destroyed between excitation pulses, and the observed signal is based on the steady-state level of longitudinal magnetization. With the refocusing sequences, the coherence of transverse magnetization is preserved. Both types use gradient-reversal echos. For use with the imaging method of the present invention it is believed to be preferable to employ sequences in which the transverse magnetization is spoiled. In T2-weighted imaging with a diamagnetic agent can improve the contrast obtained by shortened T2* effects.

The method of this invention is also believed to be applicable to multiecho MR angiography as described by Dumoulin, et al. *Mag. Res. Med.*, 5:47-57 (1987); and 6:275-286 (1988), when carried out to produce a T2* effect. This technique as described by Dumoulin, et al. has been called phase contrast angiography.

EXPERIMENTAL TESTS

The practicality of the method of this invention is shown by the following experiments.

The MRI equipment used was a General Electric CSI 2 Tesla unit with GE Acustar S-150 self-shielded gradient coils. This equipment is designed for use with "GRASS" and "EZGRASS" sequences, as well as other sequences, including Spin Echo and Echo Planar.

In the initial examination, a 10 cc bottle substantially filled with "ALBUNEX" was used as a specimen. This sample consisted of air-containing microspheres ranging in size primarily from 2 to 6 microns at a concentration of around $1 \times 10^8$ microspheres per milliliter. The amount of encapsulated air was estimated to be about 2% by volume of the "ALBUNEX" sample. A comparative sample consisted of a 10 cc glass test tube filled with tap water. These samples were subjected to a Spin Echo sequence which was T1-weighted. No differences in image intensity were observed between the two samples.

The samples were then examined by the "GE EZ-GRASS" pulse sequence with T2-weighting. The field of view was 60 mm, the TR 500 milliseconds, the TE 16 milliseconds, and the slice thickness was 1.0 cm. Images were obtained in a 20 bit resolution pixel format without frame averaging. The resulting images were transferred to a work station where the image data was scaled and converted to an eight-bit format and analyzed and formatted. Signal intensity values from this image analysis ranged from zero (white) to 255 (black). The T2-weighted "EZGRASS" image of the "ALBUNEX" sample produced a significant increase in signal loss. This signal loss was not observed from the water sample. The water sample had a signal intensity value of 56 as compared with 249 for the "ALBUNEX" sample.

The procedure was repeated with a sample in which the "ALBUNEX" microspheres had been disrupted to permit their air centers to escape leaving the albumin wall material without entrapped air. No image enhancement was observed. The disrupted "ALBUNEX" residue and the water sample were comparable. This indicated that the previously observed enhancement was caused by the air-centers of the microspheres and not by the albumin, although the amount of air present was very small (viz. about 2% of the sample volume).

An in vivo test was also conducted. A rat was anesthetized and a catheter placed in its tail vein. The rat was placed in the imaging cradle of the GE Acustar MRI unit described above. An "ALBUNEX" sample like that described above was used, 5 cc being injected slowly into the rat. An Echo Planar sequence was used with TE of approximately 16 milliseconds. Observing the rat's right heart ventricle, a decrease in signal intensity was measured due to the "ALBUNEX" of 134 as compared with 53 for the blood.

Since the foregoing tests indicated that the "ALBUNEX" samples examined by the "GE EZGRASS" pulse sequence with T2-weighting produced a loss of signal intensity, another in vitro study was carried out.

Five samples of "ALBUNEX" each with a different amount of air per ml of sample, were examined. The object was to determine whether there was a relationship between the amount of air contained in the microspheres and the magnitude of the signal loss. A GE CSI MR 2.0 T imager with a 3.5 inch (i.d.) birdcage imaging coil was used with an EZGRASS sequence (TR=200 msec, TE=1 msec, sinc power=8%, 70 mm FOV, number of excitations=4, receiver gain=64). Images were obtained in an interval of 30 to 100 seconds after the air-containing microspheres were completely dispersed. Images were obtained in a 20 bit resolution pixel format without frame averaging. The resulting images were transferred to a work station where the image data was scaled and converted to an eight-bit format and analyzed and formatted. Signal intensity values ranged from zero (white) to 255 (black). A positive essentially linear relationship was found between loss of signal intensity and the amount of air contained in the microspheres. These experiments demonstrated the importance of carrying out the magnetic resonance imaging to produce a shorted T2* effect in which the portion of the blood containing the microbubble imaging agent is contrasted by its difference in magnetic susceptibility.

We claim:
1. The method of magnetic resonance imaging (MRI), comprising the steps of:
    (a) introducing a bolus into a portion of the circulating blood of a mammal prior to or during an MRI examination, said bolus comprising an aqueous medium containing a dispersion of microspheres of diameters of less than 8 microns, said microspheres consisting of gas microbubbles encapsulated by stabilized biocompatible material, said bolus prior to administration having volume of 3.5 to 20 milliliters and a microsphere concentration of greater than $1 \times 10^6$ microspheres per milliliter; and
    (b) when the administered microspheres have reached the site to be imaged, carrying out magnetic resonance imaging by a fast imaging technique to produce a shortened T2* effect in which the portion of the blood containing the microspheres produces a decrease in signal intensity.

2. The method of claim 1 in which the imaging is carried out by an echo planar technique.

3. The method of claim 1 in which the imaging is carried out by a fast MRI technique using a series of radio frequency excitation pulses.

4. The method of claim 1 in which the imaging is carried out with a time-to-repeat (TR) of less than 100 milliseconds.

5. The method of claim 4 in which the imaging is carried out by a technique in which the coherence of transverse magnetization is spoiled.

6. The method of claims 1, 2, 3, 4, or 5 in which the microspheres consist of air microbubbles encapsulated by human serum albumin.

* * * * *